United States Patent [19]

Bürki

[11] Plant 4,816

[45] Jan. 26, 1982

[54] KALANCHOE PLANT

[75] Inventor: Moritz Bürki, Langendorf, Switzerland

[73] Assignee: Mikkelsens Inc., Ashtabula, Ohio

[21] Appl. No.: 186,277

[22] Filed: Sep. 11, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A Kalanchoe plant named Pollux, having bright red flower color and highly floriferous habit, compact growth habit, freely branching habit, relatively slow growth, adaptability to production in 10 to 15 cm. pots, and a flowering time of 11 weeks in summer up to 15 weeks in winter.

1 Drawing Figure

The present invention relates to a new and distinctive variety of kalanchoe plant, botanically known as kalanchoe, and known by the cultivar name Pollux.

The new cultivar was developed by me through controlled breeding by crossing Feuerwerk II (seed parent) with Feuerball (pollen parent). Feuerwerk II is disclosed in U.S. Plant Pat. No. 4,102, granted Sept. 13, 1977 to Adolf Grob. Feuerball is disclosed in U.S. Plant Pat. No. 3,861, granted Apr. 13, 1976 to Adolf Grob. Asexual reproduction by stem cuttings has shown that the unique features of this new kalanchoe are stabilized and are reproduced true to type in successive propagations.

The following characteristics distinguish the new kalanchoe from both its parent varieties and other cultivated kalanchoes of this type known and used in the floriculture industry:

1. Pollux was selected especially for its outstanding bright red flower color, compact growth habit, and for its freely branching ability.
2. Growth is relatively slow, being comparable to that of Feuerwerk II.
3. Freely branching, with shoots formed at every node, comparable to that of Feuerball, and much better than the branching of Feuerwerk II.
4. Proper scheduling makes Pollux suitable for production in 10 to 15 cm. pots.
5. To reduce penduncle elongation after flower initiation plants can be treated with B9.
6. Pollux is highly floriferous, with numerous flowers formed at every shoot.
7. Flowering time is approximately 11 weeks in summer to 15 weeks in winter after start of short days.

The accompanying colored photograph illustrates the overall appearance of this variety taken as a face view of the plant and showing the colors as true as it is reasonably possible to obtain in a colored reproduction of this type.

The following is a detailed description of my new kalanchoe variety based on plants produced under commercial practices in the greenhouses of Wyss Samen und Pflanzen A.G., Solothurn, Switzerland, and the greenhouses of Mikkelsens Inc., Ashtabula, Ohio. Color references are made to the Royal Horticultural Society Colour Chart except where general terms of ordinary dictionary significance are used.

Parentage: A controlled cross of the cultivar Feuerwerk II as the seed parent and the cultivar Feuerball as the pollen parent.

Propagation:

*Type cutting.*—Tip cutting with stems up to 2 cm. long.

*Time to root.*—10 days at 21° C. summer, 14 days at 21° C. winter.

*Rooting habit.*—Fibrous, very many fine roots.

PLANT DESCRIPTION

Form: Upright, short, compact. Growing and scheduling practices can produce small plants in 10 cm. pots or large plants in 15 cm. pots.

Habit of growth: Relatively slow for this type of plant. Generally, shoots are formed at every node.

Foliage description: Leaves simple, opposite, generally symmetrical, tending to be slightly folded upwards along the main vein.

*Size.*—Average full grown leaf of a flowering plant in a 10 cm. pot is 90 mm. long and 60 mm. wide.

*Shape.*—Elliptic to ovate, apex acute to obtuse, base truncate.

*Texture.*—Glabrous, coriaceous, succulent.

*Margin.*—Dentate.

*Color.*—Young foliage, top side Green 137C, under side Green 138 B-C. Mature foliage, top side Green 137 A-B, under side Green 138 B-C. Under high light conditions leaves have a red margin.

FLOWERING DESCRIPTION

Inflorescence of each shoot is formed by dichotomous branching, starting with opening of terminal flower of main axis, followed by terminal flowers of the side branches of the inflorescence. Opening of new buds will continue for two months or more. Individual flowers last two weeks or more after opening.

Natural flowering season: Late January.

Flowering time: Under controlled daylength at 20° C. in summer, 11 weeks; in winter, 15 weeks. Flowering time depends on temperature, light intensity and other growing conditions.

Flower buds: Generally oblong, up to 12 mm. long, developing to tubular as flower petals mature, sheathed with four green sepals; corolla at maturity 9 mm. long.

Flowers borne: Compound dichasial cyme. Peduncle length depends on growing conditions and B9 applications. Pedicels up to 6 mm. long.

Quantity of flowers: Very floriferous; main axis and main side shoots have 50 or more flowers, with new buds continuing to develop.

Petals:

*Shape.*—Elliptic to nearly round, apex cuspidate.

*Color.*—Top side when opening Red 44 A-B, fading to Red 44B. Under side Orange 29C, with red along the margin.

*Number of petals.*—Four, united in corolla, salverform. Total flower diameter is 18 mm.

Reproductive organs:

*Stamens.*—Eight in number. Anther shape: flat, elliptical, color yellow. Filament color: light green. Pollen color: yellow.

*Pistils.*—Stigma shape: flat, crystalline, color greenish white. Style color: light green. Ovary: 4 celled, size 7 mm. long, color green.

Disease resistance: No known kalanchoe diseases observed to date. Cultivar is highly resistant to mildew.

I claim:

1. A new and distinct cultivar of Kalanchoe plant known by the cultivar name Pollux, as described and illustrated, and particularly characterized by the combined characteristics of bright red flower color and highly floriferous habit, compact growth habit, freely branching habit, relatively slow growth, adaptability to production in 10 to 15 cm. pots, and by its flowering time of 11 weeks in summer up to 15 weeks in winter.

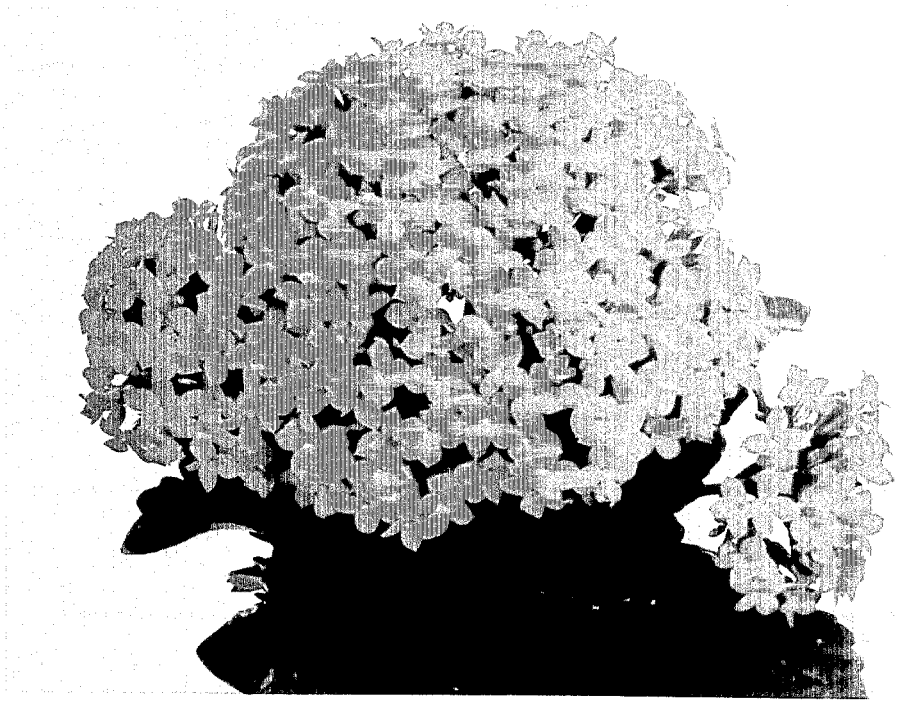

* * * * *